(12) United States Patent
Sukadhare et al.

(10) Patent No.: US 11,078,566 B2
(45) Date of Patent: Aug. 3, 2021

(54) COATINGS FOR SURGICAL INSTRUMENTS (71) Applicant: DEPUY SYNTHES PRODUCTS, INC., Raynham, MA (US)

(72) Inventors: Dayananda Sukadhare, Bayside, NY (US); Sean Selover, Westport, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 37 days.

(21) Appl. No.: 16/050,238

(22) Filed: Jul. 31, 2018

(65) Prior Publication Data

US 2018/0334741 A1 Nov. 22, 2018

Related U.S. Application Data

(62) Division of application No. 14/983,696, filed on Dec. 30, 2015, now abandoned.
(Continued)

(51) Int. Cl.
*C23C 14/06* (2006.01)
*C23C 14/02* (2006.01)
(Continued)

(52) U.S. Cl.
CPC .......... *C23C 14/0641* (2013.01); *A61L 2/232* (2013.01); *A61L 27/306* (2013.01);
(Continued)

(58) Field of Classification Search
None
See application file for complete search history.

(56) References Cited

U.S. PATENT DOCUMENTS 4,981,756 A 1/1991 Rhandhawa
5,061,238 A 10/1991 Shuler
(Continued)

FOREIGN PATENT DOCUMENTS

EP 0 590 887 B1 12/1998
WO 2006/002553 A1 1/2006
(Continued)

OTHER PUBLICATIONS

Kelly et al. A study of the antimicrobial and tribiological properties of TiN/Ag nanocomposite coatings. Surface and Coatings Technology vol. 204, issue 6-7 pp. 1137-1140. Dec. 25, 2009 (Year: 2009).*
(Continued)

*Primary Examiner* — Cachet I Proctor
(74) *Attorney, Agent, or Firm* — Barnes & Thornburg, LLP (57) ABSTRACT

A coated medical instrument can include a first layer bonded to a metal substrate surface of a medical instrument, a second layer bonded to the first layer, and a third layer disposed on the second layer, The first layer comprises chromium (Cr), hafnium (Hf), titanium (Ti), and/or niobium (Nb). The second layer comprises a nitride, oxide, carbide, carbonitride, or boride of chromium (Cr), hafnium (Hf), niobium (Nb), tungsten (W), titanium (Ti), aluminum (Al), zirconium (Zr), and/or silicon (Si). The third layer comprises a nitride, oxide, carbide, boride, oxynitride, oxycarbide, or oxycarbonitride of chromium (Cr), hafnium (Hf), niobium (Nb), tungsten (W), titanium (Ti), aluminum (Al), zirconium (Zr), and/or silicon (Si). Methods for making coated medical instruments are also disclosed herein.

13 Claims, 5 Drawing Sheets

Related U.S. Application Data (60) Provisional application No. 62/097,755, filed on Dec. 30, 2014.

(51) Int. Cl.

| | | |
|---|---|---|
| *C23C 14/32* | (2006.01) | |
| *C23C 14/08* | (2006.01) | |
| *C23C 14/00* | (2006.01) | |
| *A61L 2/232* | (2006.01) | |
| *A61L 27/30* | (2006.01) | |
| *A61L 31/08* | (2006.01) | |

(52) U.S. Cl.
CPC ........ *A61L 31/082* (2013.01); *C23C 14/0068* (2013.01); *C23C 14/0089* (2013.01); *C23C 14/022* (2013.01); *C23C 14/083* (2013.01); *C23C 14/325* (2013.01); *A61L 2420/08* (2013.01); *A61L 2430/38* (2013.01)

(56) References Cited

U.S. PATENT DOCUMENTS

| | | | |
|---|---|---|---|
| 5,152,774 A * | 10/1992 | Schroeder | A61B 17/3201 |
| | | | 148/537 |
| 5,308,311 A | 5/1994 | Eggers et al. | |
| 5,347,887 A | 9/1994 | Rosenthal et al. | |
| 5,549,604 A | 8/1996 | Sutcu et al. | |
| 5,925,039 A | 7/1999 | Landingham | |
| 6,330,750 B1 | 12/2001 | Meckel | |
| 6,440,150 B1 | 8/2002 | Hipp et al. | |
| 6,500,187 B1 | 12/2002 | Petersen | |
| 6,656,186 B2 | 12/2003 | Meckel | |
| 7,396,408 B2 | 7/2008 | Schreck et al. | |
| 7,992,309 B2 | 8/2011 | Fleming et al. | |
| 7,998,158 B2 | 8/2011 | Fletcher et al. | |
| 8,394,473 B2 | 3/2013 | McCrea et al. | |
| 8,663,819 B2 | 3/2014 | Gonzalez et al. | |
| 2002/0151393 A1 * | 10/2002 | Liechty, II | F42B 6/08 |
| | | | 473/578 |
| 2007/0082229 A1 | 4/2007 | Mirchandani et al. | |
| 2007/0123920 A1 | 5/2007 | Inokuti et al. | |
| 2007/0202361 A1 * | 8/2007 | Frauchiger | A61L 31/082 |
| | | | 428/701 |
| 2008/0027431 A1 | 1/2008 | Williams et al. | |
| 2009/0297720 A1 | 12/2009 | Ramgopal et al. | |
| 2010/0119819 A1 | 5/2010 | Rodgers et al. | |
| 2010/0304065 A1 | 12/2010 | Tomantschger et al. | |
| 2011/0054633 A1 | 3/2011 | Miller et al. | |
| 2011/0287223 A1 | 11/2011 | Victor et al. | |
| 2012/0006785 A1 | 1/2012 | Gorokhovslcy et al. | |
| 2012/0035739 A1 * | 2/2012 | Wilhemsson | A61F 2/30767 |
| | | | 623/23.53 |
| 2012/0276826 A1 | 11/2012 | Floter et al. | |
| 2013/0143022 A1 | 6/2013 | Schreck et al. | |
| 2014/0018801 A1 | 1/2014 | Yeh et al. | |
| 2014/0171924 A1 * | 6/2014 | Janssen | C23C 14/0641 |
| | | | 606/1 |
| 2014/0178584 A1 | 6/2014 | Zhuk et al. | |
| 2014/0255722 A1 | 9/2014 | Nagarajan et al. | |
| 2016/0186307 A1 | 6/2016 | Sukadhare et al. | |

FOREIGN PATENT DOCUMENTS

| | | |
|---|---|---|
| WO | 2010/077204 A1 | 7/2010 |
| WO | 2010/141461 A1 | 12/2010 |
| WO | 2012/167063 A1 | 12/2012 |

OTHER PUBLICATIONS

Yuan et al. Protection properties of TiN coating prepared by Arc Ion Plating and Magnetron Sputtering on TC11 Titanium Alloy. Journal of Iron and Steel Research International. vol. 11, Issue 5 Supplement 1, Sep. 2007, pp. 142-146 (Year: 2007).*

Ewald et al. Antimicrobial titanium/silver PVD coatings on titnaium. Biomedical Engineering OnLine 2006. (Year: 2006).*

International Search Report for Application No. PCT/US2015/067782, dated Jul. 1, 2016 (11 pages).

* cited by examiner

FIG. 5A CrN THIN 3.8 μm
FIG. 5B CrN THICK 7.3 μm
FIG. 5C NbO 3.0 μm
FIG. 5D HfO 4.8 μm
FIG. 5E HfN 3.0 μm
FIG. 5F NbN 3.4 μm

FIG. 6A  CrN THIN HF1
FIG. 6B  CrN THICK HF2.3
FIG. 6C  NbO HF2.3
FIG. 6D  NbO HF4
FIG. 6E  HfN HF1-2
FIG. 6F  NbN HF2

COATINGS FOR SURGICAL INSTRUMENTS

CROSS-REFERENCE TO RELATED APPLICATIONS

This application is a divisional of U.S. Non-Provisional application Ser. No. 14/983,696, filed Dec. 30, 2015, which claims priority to U.S. Provisional Application No. 62/097,755, filed on Dec. 30, 2014 and entitled "Coating for Surgical Instruments," each of which are hereby incorporated by reference in its their entirety.

FIELD

The present application relates to coatings and methods for forming the same, for example, coatings for a surgical instrument.

BACKGROUND OF THE INVENTION

There are many types of surgical instruments used to perform surgical procedures in hospitals or other medical facilities. Overtime, these surgical instruments can experience wear and/or be damaged. For example, medical personnel such as doctors and nurses, often repeatedly handle a surgical instrument during a given surgical procedure. At the same time, the surgical instrument can be exposed to air and various bodily fluids which can cause spotting, staining, and/or corrode the instrument. After a surgical procedure has been completed, the instruments are typically cleaned and sterilized so that they can be reused for a subsequent surgical procedure.

While hospitals and/or the individual physicians can reduce costs by cleaning and reusing surgical instruments, the cleaning and sterilization processes can shorten an instrument's useful life. A surgical instrument is typically formed from one or more metals (e.g., stainless steel). Stainless steel is commonly used to produce surgical instruments and is a metal alloy that generally includes iron, carbon, chromium, nickel, manganese, silica, and other metals. Stainless steel and many other metals/metal alloys are likely to corrode from normal use. Protracted and repeated handling of a metal instrument can cause a metal instrument to corrode more quickly, as can cleaning and/or sterilization processes.

Conventional surgical instruments formed from metal are not easily identifiable because they generally have the same silver color. During a surgical procedure, it is important for a surgeon and other medical personnel to identify and distinguish between multiple types and/or sized instruments placed on a surgical tray. The selection of the correct instrument should be made quickly as a delay could increase the duration of the procedure and the associated risks to the patient. However, surgical instruments are typically made from stainless steel and tend to have a similar color, making it difficult for medical personnel to quickly and easily visually identify and select the desired instrument.

Accordingly, there is a need for durable, corrosion-resistant, and easily identifiable surgical instruments.

SUMMARY OF THE INVENTION

Coated surgical instruments are described which utilize coatings to improve the corrosion-resistance and/or impart other desirable properties to the instrument (e.g., color, appearance). An uncoated surgical instrument can be formed from a variety of materials, such as varying grades of stainless steel. The instrument can be coated with one or more layers of material and/or material gradients. The composition, thickness, and technique for forming each layer can be selected to impart a specific property on the instrument, such as to improve the instrument's corrosion resistance. A corrosion-protection layer, for example, can have a higher resistance to corrosion than the untreated instrument, e.g., uncoated stainless steel. By way of example, a surgical instrument can be coated with two or more layers, such as a base layer and corrosion-protection layer/gradient. In some embodiments, the instrument can have a top layer deposited onto the corrosion-protection layer and this outer layer can have a distinctive color so that a user can more easily visually identify the instrument.

Methods for depositing coatings onto a surgical instrument are also described. Distinct coating sequences can be carried out using any combination of vapor deposition and coating systems. The methods can generally begin by pre-cleaning the uncoated/untreated instrument prior to depositing coatings or material gradients. While the techniques for coating the instrument can vary, in one example, a first vapor deposition system can be used to sequentially deposit the first metal layer and the corrosion-protection layer onto the surgical instrument and a second vapor deposition system can be used to deposit a third, outer layer onto the metal compound layer/gradient. The manufacturing methods herein can provide greater flexibility in selecting and depositing particular coatings and/or material gradients onto a surgical instrument.

In various aspects, a coated medical instrument comprises a first layer bonded to a metal substrate surface of a medical instrument, a second layer bonded to the first layer, and a third layer disposed on the second layer. The first layer comprises chromium (Cr), hafnium (Hf), titanium (Ti), and/or niobium (Nb). The second layer comprises a nitride, oxide, carbide, carbonitride, or boride of chromium (Cr), hafnium (Hf), niobium (Nb), tungsten (W), titanium (Ti), aluminum (Al), zirconium (Zr), and/or silicon (Si). The third layer comprises a nitride, oxide, carbide, boride, oxynitride, oxycarbide, or oxycarbonitride of chromium (Cr), hafnium (Hf), niobium (Nb), tungsten (W), titanium (Ti), aluminum (Al), zirconium (Zr), and/or silicon (Si).

In various aspects, a method for manufacturing a coated medical instrument comprises depositing a first layer on a metal substrate surface of a medical instrument by vapor deposition, depositing a second layer on the first layer by vapor deposition, and depositing a third layer on the second layer by vapor deposition. The first layer comprises chromium (Cr), hafnium (Hf), titanium (Ti), and/or niobium (Nb). The second layer comprises a nitride, oxide, carbide, carbonitride, or boride of chromium (Cr), hafnium (Hf), niobium (Nb), tungsten (W), titanium (Ti), aluminum (Al), zirconium (Zr), and/or silicon (Si). The third layer comprises a nitride, oxide, carbide, boride, oxynitride, oxycarbide, or oxycarbonitride of chromium (Cr), hafnium (Hf), niobium (Nb), tungsten (W), titanium (Ti), aluminum (Al), zirconium (Zr), and/or silicon (Si).

The first layer can be 0.01 to 1.0 microns thick; the second layer can be 1.0 to 5.0 microns thick; and/or the third layer can be 0.01 to 5.0 microns thick. The first layer can be about 0.01, 0.05, 0.1, 0.2, 0.3, 0.4, 0.5, 0.6, 0.7, 0.8, 0.9, or 1.0 microns thick. The first layer can be 0.01 to 0.1, 0.1 to 1.0, 1.0 to 2.0, 2.0 to 3.0, 3.0 to 4.0, or 4.0 to 5.0 microns thick. The second layer can be about 1.0, 1.5, 2.0, 2.5, 3.0, 3.5, 4.0, 4.5, or 5.0 microns thick. The second layer can be about 1.0 to 2.0, 2.0 to 3.0, 3.0 to 4.0, or 4.0 to 5.0 microns thick. The third layer can be 0.01 to 5.0 microns thick. The third layer can be about 0.01, 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 microns thick. The third layer can be about 0.01 to 0.1, 0.1 to 1.0, 1.0 to 2.0, 2.0 to 3.0, 3.0 to 4.0, or 4.0 to 5.0 microns thick.

The first layer can comprise metallic Cr, Hf, Ti, or Nb or a nitride or oxide of Cr, Hf, Ti, or Nb. The first layer can be metallic Cr, Hf, Ti, or Nb. The first layer can be a nitride of Cr, Hf, Ti, or Nb. The first layer can be an oxide of Cr, Hf, Ti, or Nb.

The second layer can comprise a nitride or oxide of Cr, Hf, Nb, W, Ti, Al, Zr, or Si. The second layer can be a nitride of Cr, Hf, Nb, W, Ti, Al, Zr, or Si. The second layer can be an oxide of Cr, Hf, Nb, W, Ti, Al, Zr, or Si.

The third layer can comprise Ti. The third layer can be a nitride, oxide, carbide, boride, oxynitride, oxycarbide, or oxycarbonitride of titanium (Ti).

The third layer can be blue, grey, or black.

The metal substrate surface can be stainless steel.

The second layer can have a monoblock, multilayered, or gradient structure (e.g., a gradient structure formed by utilizing different metal targets, power settings within the system and/or gas, gas mixtures and ratios).

The coated medical instrument can include: a first layer that comprises metallic Cr and a second layer comprises a nitride or oxide of Cr; a first layer that comprises metallic Hf and a second layer that comprises a nitride or oxide of Hf; or a first layer that comprises metallic Nb and the second layer comprises nitride or oxide of Nb. The nitride or oxide of Cr, Hf, or Nb can comprise a gradient structure.

The coated medical instrument can be corrosion resistant (e.g., in normal, saline, and/or aqueous environments).

The coated medical instrument can be a spine surgical instrument. The coated medical instrument can be a spinal implant.

At least one of the layers can be deposited by an arc process or a combination of an arc and sputter processes.

At least one of the layers can be deposited at a temperature of 180 to 1,000° F. The deposition temperature can be about 180, 200, 300, 400, 500, 600, 700, 800, 900, or 1,000° F. The deposition temperature can be about 180 to 200, 200 to 300, 300 to 400, 400 to 500, 500 to 600, 600 to 700, 700 to 800, 800 to 900, or 900 to 1,000° F.

The method can include a reactive plasma surface cleaning-conditioning process before depositing at least one of the first, second, and third layers. The method can include a reactive plasma surface cleaning-conditioning process before depositing all three of the first, second, and third layers. The method can include a reactive plasma surface cleaning-conditioning process before depositing the first and third layers.

The method can include an external cleaning of the metal substrate surface before depositing the first layer.

The method can include depositing the second layer using an arc and sputter process, thereby depositing a gradient in the second layer.

The method can include depositing the first and second layers in a first vapor deposition chamber and depositing the third layer in a second vapor deposition chamber.

The method can include cleaning and conditioning a surface of the second layer using a plasma cleaning technique before depositing the third layer.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Coated surgical instruments are described which utilize one or more layers of coating to improve the corrosion-resistance and/or impart other desirable properties to the instrument. An uncoated surgical instrument can be formed from a variety of materials, such as varying grades of stainless steel. The instrument can be coated with one or more layers of material. For example, one or more layers of material and/or material gradients can be deposited onto an outer surface of the instrument. The composition, thickness, and technique for forming each layer can be selected to impart a specific property on the instrument, such as to improve the instrument's corrosion resistance. A corrosion-protection layer, for example, can have a higher resistance to corrosion than the untreated instrument, e.g., uncoated stainless steel. By way of example, a surgical instrument can be coated with two or more layers, such as a base layer and corrosion-protection layer/gradient. In some embodiments, the instrument can have a top layer deposited onto the corrosion-protection layer and this outer layer can have a distinctive color so that a user can more easily visually identify the instrument.

Methods for depositing coatings onto a surgical instrument are also described. Distinct coating sequences can be carried out using any combination of vapor deposition and coating systems. The methods can generally begin by pre-cleaning the uncoated/untreated instrument prior to depositing coatings or material gradients. While the techniques for coating the instrument can vary, in one example, a first vapor deposition system can be used to sequentially deposit the first metal layer and the corrosion-protection layer onto the surgical instrument and a second vapor deposition system can be used to deposit a third, outer layer onto the metal compound layer/gradient. The manufacturing methods herein can provide greater flexibility in selecting and depositing particular coatings and/or material gradients onto a surgical instrument.

Techniques for Pre-Cleaning an Instrument

Prior to depositing a coating onto an instrument, an untreated instrument can be subjected to a pre-cleaning process that will prepare the surface for receiving one or more layers/gradients. At least one of the following methods can be used for providing a substrate having a clean surface (e.g., capable of electrical conduction): compressed air blow-off, chemical cleaning, electrolytic cleaning, grinding, polishing, tumbling, blasting, solvent degreasing, and ultrasonic cleaning. As will be appreciated, other known cleaning techniques can be used to prepare the substrate of the instrument.

Coating Structure

Any number of coatings can be deposited onto a surgical instrument to improve one or more of the performance and/or other characteristics of the instrument.

Figure 1A:
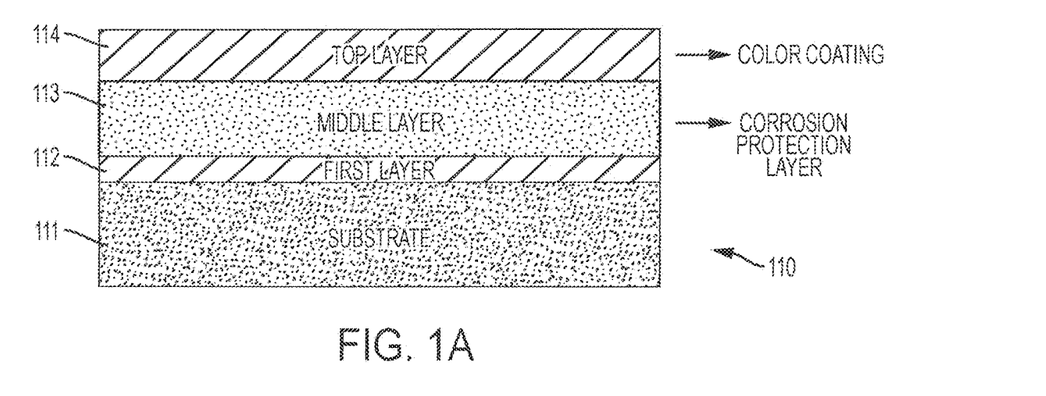
FIG. 1A illustrates a gradient or one mono-block coating structure.
Figure 1B:
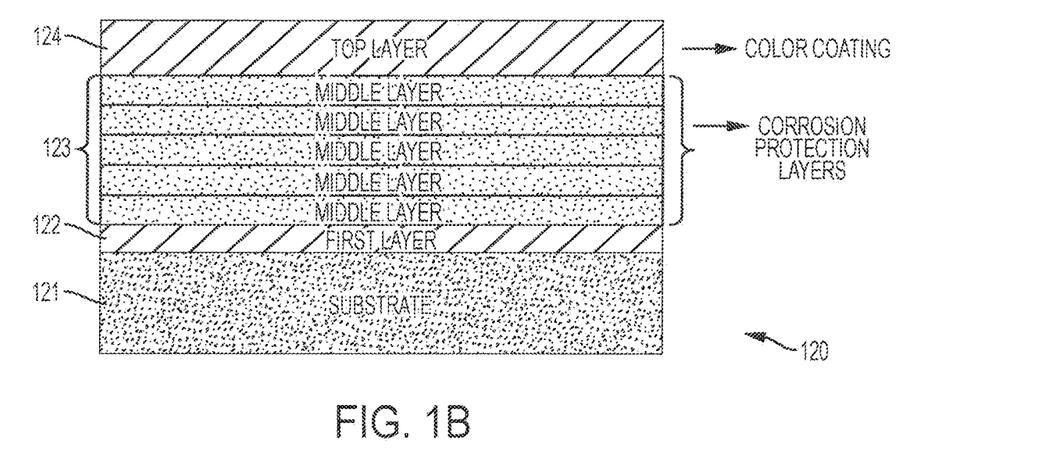
FIG. 1B illustrates a multi/nanolayer stack coating structure.

As illustrated in FIGS. 1A and 1B, a coated medical instrument 110, 120 comprises a first layer 112, 122 bonded to a metal substrate 111, 121 surface of a medical instrument, a second layer 113, 123 bonded to the first layer, and a third layer 114, 124 disposed on the second layer. The metal substrate surface can be steel, or more particularly a stainless steel (e.g., surgical grade stainless steel).

The first layer 112, 122 comprises chromium (Cr), hafnium (Hf), titanium (Ti), and/or niobium (Nb). The second layer 113, 123 comprises a nitride, oxide, carbide, carbonitride, or boride of chromium (Cr), hafnium (Hf), niobium (Nb), tungsten (W), titanium (Ti), aluminum (Al), zirconium (Zr), and/or silicon (Si). The third layer 114, 124 comprises a nitride, oxide, carbide, boride, oxynitride, oxycarbide, or oxycarbonitride of chromium (Cr), hafnium (Hf), niobium (Nb), tungsten (W), titanium (Ti), aluminum (Al), zirconium (Zr), and/or silicon (Si).

In some examples, the first layer can comprise metallic Cr, Hf, Ti, or Nb or a nitride or oxide of Cr, Hf, Ti, or Nb. The first layer can be metallic Cr, Hf, Ti, or Nb. The first layer can be a nitride or oxide of Cr, Hf, Ti, or Nb. The second layer can comprise a nitride or oxide of Cr, Hf, Nb, W, Ti, Al, Zr, or Si. The second layer can be a nitride of Cr, Hf, Nb, W, Ti, Al, Zr, or Si. The second layer can be an oxide of Cr, Hf, Nb, W, Ti, Al, Zr, or Si. The third layer can comprise Ti. The third layer can be a nitride, oxide, carbide, boride, oxynitride, oxycarbide, or oxycarbonitride of titanium (Ti).

As described in connection with the experimental examples below, the coated medical instrument can include: a first layer that comprises metallic Cr and a second layer comprises a nitride or oxide of Cr; a first layer that comprises metallic Hf and a second layer that comprises a nitride or oxide of Hf; or a first layer that comprises metallic Nb and the second layer comprises nitride or oxide of Nb. The nitride or oxide of Cr, Hf, or Nb can comprise a gradient structure.

The first two layers can impart corrosion resistance to the coated medical instrument. The third layer may also impart corrosion resistance and/or color (e.g., blue, grey, or black) to the coated medical instrument.

The layers can have a mono block, gradient, and/or layered structure. For example, the second layer 113 can be a monoblock or gradient structure. Alternatively, the second layer 123 can be a layered structure. Although not expressly illustrated in FIGS. 1A and 1B, a first and/or third layer can have a gradient or layered structure. As will be understood by those skilled in the art, gradient structures can be formed, e.g., by utilizing different metal targets, power settings within the system and/or gas, gas mixtures and ratios.

In another example, a surgical instrument can include a base (e.g., first) layer and a middle (e.g., second) layer. The base layer can be deposited onto a surface of a pre-cleaned instrument, as mentioned above, and the middle layer can be deposited onto the base layer. These two layers can improve the corrosion resistance of the instrument. The base layer can be a metallic layer of Chromium (Cr) or Niobium (Nb) which can be deposited by a vapor deposition method followed by a middle layer which can be a metal nitride, carbide, carbo-nitride, or boride. The middle layer can include at least one of the following metals, Chromium (Cr), Hafnium (Hf), Niobium (Nb), Tungsten (W) and Zirconium (Zr), and the metals may be in a compound form.

A top layer, such as a third layer in the case of coatings that include a base layer and middle layer, can be deposited onto one or more corrosion-resistant layers and this layer can impart a distinctive color to the instrument. The top layer can include at least one of the following metals including Chromium, Hafnium, Niobium, Tungsten, Zirconium, Aluminum (Al), Silicon (Si), and Titanium (Ti). The structure of this coating may be a carbide, nitride, carbo-nitride, oxy carbo nitride, oxy nitride, oxy carbide, or boride, of any of the metals named above. For example, the top layer can be a pre-determined shade of black (or another color such as blue or grey).

The thickness of the layers can also vary. The first layer can be 0.01 to 1.0 microns thick; the second layer can be 1.0 to 5.0 microns thick; and/or the third layer can be 0.01 to 5.0 microns thick. The first layer can be about 0.01, 0.05, 0.1, 0.2, 0.3, 0.4, 0.5, 0.6, 0.7, 0.8, 0.9, or 1.0 microns thick. The first layer can be 0.01 to 0.1, 0.1 to 1.0, 1.0 to 2.0, 2.0 to 3.0, 3.0 to 4.0, or 4.0 to 5.0 microns thick. The second layer can be about 1.0, 1.5, 2.0, 2.5, 3.0, 3.5, 4.0, 4.5, or 5.0 microns thick. The second layer can be about 1.0 to 2.0, 2.0 to 3.0, 3.0 to 4.0, or 4.0 to 5.0 microns thick. The third layer can be 0.01 to 5.0 microns thick. The third layer can be about 0.01, 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 microns thick. The third layer can be about 0.01 to 0.1, 0.1 to 1.0, 1.0 to 2.0, 2.0 to 3.0, 3.0 to 4.0, or 4.0 to 5.0 microns thick. In another example, the base layer/gradient can be in the range of about 0.1-1 micron thick, the middle layer can be in the range of about 1-5.0 microns thick, and the top layer can be in the range of about 0.1-5.0 microns thick.

As will be described in greater detail below, the layers of material can be deposited onto the surgical instrument using various techniques. For example, in one embodiment, the layers can be deposited using a vapor deposition method with the base and middle coats deposited onto the instrument in a first vapor deposition device and the final top coat layer being deposited onto the instrument using a second vapor deposition device.

Vapor Deposition Techniques for Coating an Instrument

In various aspects, a method for manufacturing a coated medical instrument comprises depositing a first layer on a metal substrate surface of a medical instrument by vapor deposition, depositing a second layer on the first layer by vapor deposition, and depositing a third layer on the second layer by vapor deposition.

Figure 2:
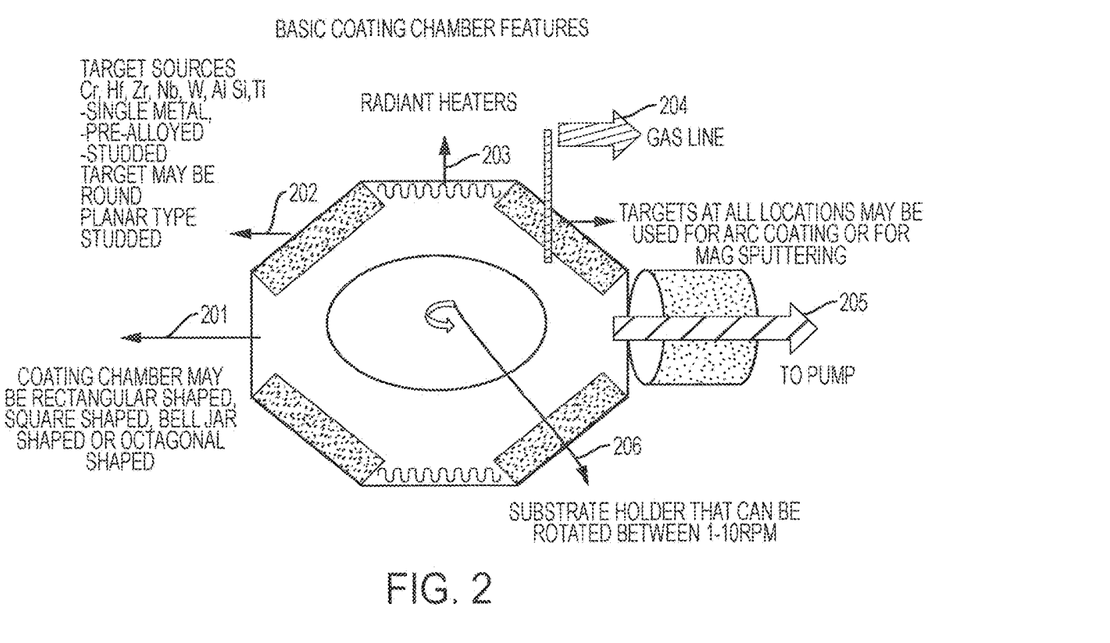
FIG. 2 illustrates am exemplary coating chamber.
Figure 3:
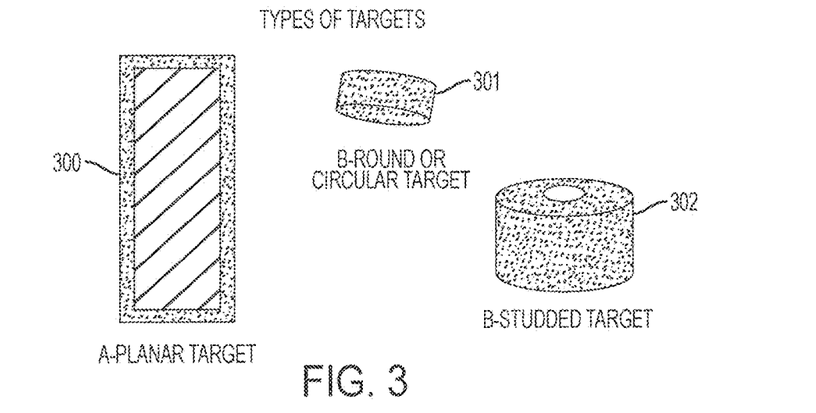
FIG. 3 illustrates different types of targets.

FIG. 2 illustrates an exemplary vapor deposition device 200 that can be used to deposit one or more layers/gradients of metal coating onto a surgical instrument. The vapor deposition device coating chamber 201 can be used in a square shaped, rectangular shaped, octagonal shaped, or a simple bell jar shaped, made from stainless steel. The coating system can have arc sources and/or sputter sources (illustrated here as target sources 202) positioned at strategic locations of the walls and the system can have planar, round, or studded targets of standard sizes. The targets can be of a single metal composition or studded or pre-alloyed with binary or ternary alloys of different metals or compounds of Chromium, Hafnium, Tungsten, and Niobium, Zirconium, Aluminum, Silicon and Titanium, as shown in FIG. 3. The deposition device 200 also includes radiant heaters 203, gas line 204, pump line 205 to create a vacuum, and a substrate holder 207 (e.g., which can be rotated 1 to 10 RPM, or any other rotational value or range discussed herein).

Although vapor deposition device 200 is presented as an example for illustrative purposes, one skilled in the art will understand that the invention can be implemented in various other vapor deposition devices in view of the disclosure provided herein.

As discussed above, the method can include a reactive plasma surface cleaning-conditioning process before depositing at least one of the first, second, and third layers. The method can include a reactive plasma surface cleaning-conditioning process before depositing all three of the first, second, and third layers. The method can include a reactive plasma surface cleaning-conditioning process before depositing the first and third layers. The method can include an external cleaning of the metal substrate surface before depositing the first layer.

The in situ etch process can include a glow discharge process utilizing Hydrogen or Argon plasma or an arc-triggered glow discharge process using Argon, Hydrogen, and Nitrogen, or a combination thereof. The substrate can be capable of being rotated and electrically biased. The bias for the arc coating system can be a DC bias or a pulsed DC bias or a combination thereof. Appropriate power sources can be used for arc or magnetron sputtering. The arc system utilized can be a filtered arc method utilizing a magnetic array of filters in situ the chamber to attain cleaner and denser coatings.

At least one of the layers can be deposited by an arc process or a combination of an arc and sputter processes. For example, a method of applying a vapor deposited coatings in an environment where the deposition process used may be predominantly a cathodic arc method or a combination of a cathodic arc and sputter processes can include applying the various layers in two distinct systems at temperatures in the range of about 180-1000° F. More particularly, the deposition temperature can be about 180, 200, 300, 400, 500, 600, 700, 800, 900, or 1,000° F. The deposition temperature can be about 180 to 200, 200 to 300, 300 to 400, 400 to 500, 500 to 600, 600 to 700, 700 to 800, 800 to 900, or 900 to 1,000° F. The method can be performed using the above mentioned arc/sputter systems to produce a coating architecture of a specific thickness and formed from specific compounds.

The sputter technique used can be of reactive sputter type. Where the metal is sputtered, the compound can be formed on the instrument surface using one or more gasses such as Argon, Nitrogen, Acetylene, Oxygen, or Methane.

A combination of different source target compositions within the said process can be used as one of the elements to obtain the desired coating architecture on the instrument. The two vapor coating devices can make use of various gasses using at least one of the following gasses to enable formation of the metal compound on the instrument: Argon, Nitrogen, Methane, Acetylene and Oxygen.

The vapor device systems shown have arc sources and sputter sources at strategic locations on the walls of the coating device. The arc sources can be a planar target 300 or a round target 301 of standard sizes or a studded target 302 with two different metals, as illustrated in FIG. 3. The targets can be a single metal type, binary, or ternary alloys or compounds of the metals, Chromium, Hafnium, Niobium, Tungsten, Silicon, Aluminum, or Titanium. The studded targets can include two metals press fitted into each other.

A method of applying a coating on spinal instruments can include pre-cleaning the surface of the instrument, as detailed above, before loading the instrument onto fixtures that are in turn loaded into a series of vacuum systems for different stages (layers) of the coating. An internal surface etch process can be used to enhance adhesion the base metal coat or subsequent layers can be deposited over each other using a glow discharge or ion bombardment process that allows for a surface cleaning-etching process that enables a superior adhesion of the coating to the substrate.

A method of achieving said coating architecture-sequence can involve a two step coating sequence or coating operations. The two coating steps in the two different devices that deposit the bottom and middle layers and the top layer will involve pre-cleaning before coating via an external cleaning method.

The in situ etch process may include a glow discharge process utilizing Hydrogen or Argon plasma or an arc triggered glow discharge arc process using Argon, Hydrogen and Nitrogen or a combination thereof. The bias for the arc coating system may be a DC bias or a pulsed DC bias or a combination thereof. Radiant heaters can be used to heat the instrument to a temperature in the range of about 180-1000° F., or a different temperature range or value discussed herein.

A method of achieving a said coating architecture-sequence can involve a two-step coating sequence or coating operation. The two coating steps can be carried out in the two different devices—one that coats the first and middle (second) layer and the second that coats the top (third) layer. Between the two steps there can be physical transfer of thee substrates between the two devices and can involve a pre-cleaning step before the top layer coating is applied.

Different fixturing methods can be used for the type of product utilizing metallic masking wherever required. The scope of fixturing may utilize a single, double or even triple planetary for uniform deposition in either the arc or sputter systems. Rotational speeds in the range of about 1 to 10 RPM, or lower, e.g., 0.2-10.0 RPM, can be utilized for etching/coating/cooling sequences. For example, a rotation speed can be 0.2, 0.3, 0.4, 0.5, 0.6, 0.7, 0.8, 0.9, 1, 2, 3, 4, 5, 6, 7, 8, 9, or 10 RPM. A rotation speed can be in the range of 0.2 to 1, 1 to 2, 2 to 3, 3 to 4, 4 to 5, 5 to 6, 6 to 7, 7 to 8, 8 to 9, or 9 to 10 RPM.

Figure 4:
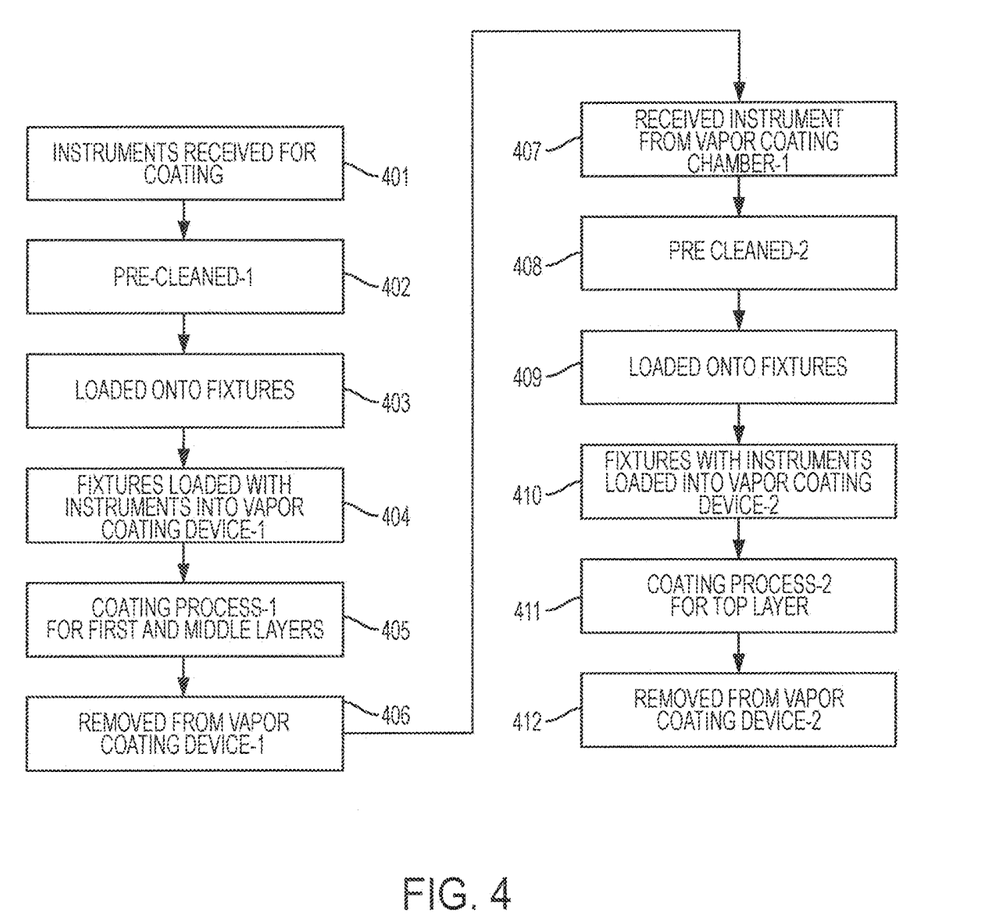
FIG. 4 is a flow chart for a multi-chamber coating process.

An exemplary overall process 400 of coating a surgical instrument is shown in FIG. 4. The process 400 utilizes two reaction chambers (referred to as chamber 1 and chamber 2).

In step 401, an instrument is received for coating/cleaning. For example, one or more surgical instruments can be loaded onto the fixtures and can be stacked for pre-cleaning. Step 402 of (first) pre-cleaning can be achieved by at least one of the several methods described above such as compressed air blow offs, chemical cleaning, electrolytic cleaning, grinding, polishing, tumbling, blasting, solvent degreasing and other forms of ultrasonic cleaning using various solvents and solutions.

In step 403, an instrument is loaded onto fixtures and in step 404 the fixtures are loaded into vapor coating device 1 (the first coating chamber). For example, after pre-cleaning is complete, the instrument(s) can be loaded in pre-designed orientations for coating. Areas of the instrument that may require masking can be masked using predesigned fixtures.

Once the loading is complete, the coating device can be considered ready for the next step of loading for the purposes of conditioning and coating. The overall process can include a pump down cycle to create a vacuum within the coating system and the tools are next subjected to pre heating in the presence of radiant heaters. Once a satisfactory level of vacuum is reached, the radiant heaters within the system can be turned on to preheat the substrate (e.g., instrument+fixtures).

Conditioning of the substrate inclusive pre cleaning and etching of the substrate surface (e.g., instruments+fixtures) can be carried out by creating a plasma using a target and at least one of argon, hydrogen, and oxygen. At least one target (e.g., Cr or Ti) can be used.

Etching can be carried out using one of many gasses or combinations. At least one of the following gasses can be used, including Argon, Hydrogen, and Nitrogen. The etching process can be a plasma process where the surgical instruments are biased and the arc is stuck with the target and the biased tool using any/or all of the gasses named above. During etching, the instruments in the fixtures are rotated in the vapor device in the range of about 1-10 RPM, or another rotational value or range disclosed herein.

Step 405 includes coating the instrument (coating process 1, for the first and second layers). Coating in vapor coating device 1 can be accomplished using an arc process or a sputter process under predetermined conditions of target compositions, configurations and orientations to the tool presenting themselves in the chamber. The process can utilize at least one of Argon, Nitrogen, methane, acetylene and oxygen, but multiple gases can be used in tandem. The coating can use a straight DC bias or a pulsed DC bias. Different targets subject to electrical charging can have different chemical compositions and can be used together with other targets or at different stages of the coating sequence. Adequate electromagnetic filtering can be utilized during the coating sequence to avoid un-ionized metal droplets from contaminating the coating on the tool. During coating, the surgical instruments can be heated to facilitate uniform coating on the instrument, but should not be heated high enough so as to soften or otherwise damage the structural integrity of the surgical instrument. Once the surgical instrument is coated to satisfy the coating architecture described above, the electrical circuits and the gasses are switched off and the tools cooled. After the temperature of the instrument has decreased to about 120° F. (or lower), the instrument(s) can be removed from the chamber/coating device 1 (step 406).

In step 407, the instrument is received from stage 1 coating. The surgical instruments can then be pre-cleaned (step 408) and loaded onto fixtures (step 409). The fixtures are the loaded into vapor coating device 2 (a second chamber) in step 410. The pre-cleaning may include at least one cleaning method selected from the group consisting of compressed air blow-offs, chemical cleaning, electrolytic cleaning, grinding, polishing, tumbling, blasting, solvent degreasing and other forms of ultrasonic cleaning using various solvents and solutions.

Pre-etching of the surfaces of the pre-coated instrument as received from vapor deposition device 1 can be performed using a plasma cleaning technique, similar to the methods used in vapor deposition chamber 1. The basic structure of the vacuum chamber can be similar to vapor device 1 in terms of target types, locations, etc., but may include the ability to form additional compounds of the third layer of the invention on the tools, such a nitride, oxide, carbide, boride, oxynitride, oxycarbide, or oxycarbonitride of chromium (Cr), hafnium (Hf), niobium (Nb), tungsten (W), titanium (Ti), aluminum (Al), zirconium (Zr), and/or silicon (Si). The third layer can provide a distinctive color coating.

In step 411, the instrument is coated with a third layer according to the invention. After the coating is complete, the instrument can be removed from the coating chamber (step 412) and packaged (optional, not shown).

Corrosion Testing

In various embodiments, the coated medical instrument is corrosion resistant. Corrosion resistance can be tested and/or quantified by methods known in the art. A corrosion test can be a pass/fail test, for example a tester can conduct a visual inspection for corrosion with any visually detected corrosion considered a failed test (e.g., not corrosion resistant) and an absence of visual corrosion considered a passed test (e.g., corrosion resistant). Corrosion resistance can be measured using conditions that replicate or simulate clinical sterilization and/or use. Corrosion resistance can be corrosion resistance in normal, saline, and/or aqueous environments.

One example corrosion test is as follows:

Materials: 1. coated medical instruments or test coupons (e.g., produced according to the invention, illustrated in Example 1); 2. cleanser, such as Steris Instru-Klenz Alkaline Instrument Cleaner (108608), diluted to twice the recommended concentration (2%); and 3. a brush, such as a toothbrush (Oral-B Soft 30).

Methods: Autoclave the test coupons for one cycle, check for corrosion. Soak test coupons in Steris Instru-Klenz solution for 10 minutes, rinse in water, then scrub surface for 1 minute. Autoclave the sample 25 times and check for corrosion after the 5th and 25th cycles. Soak test coupons in Steris Instru-Klenz solution again, rinse in water, then scrub surface for 1 minute. Autoclave 50 more times, check for corrosion (e.g., by visual inspection) after the 25th and 50th cycles.

EXAMPLES

Example 1

Corrosion Resistant Layer Preparation

Stainless steel coupons having a CrN thin film coating (Cr first layer, CrN second layer), CrN thick film coating (Cr first layer, CrN second layer), NbO coating (Nb first layer, NbO second layer), HfO coating (Hf first layer, HfO second layer), HfN coating (Hf first layer, HfN second layer), and NbN coating (Nb first layer, NbN second layer) were prepared according to the methods described above. The CrN thin film and CrN thick film coatings (Set Nos. 1 and 3) were produced using reactive cathodic arc (RCA) technology. The NbO, HfO, HfN, and NbN coatings (Set Nos. 2 and 4-6) were produced using reactive magnetron sputtering (RPMS or suputtering) technology.

TABLE 1

Six example coatings according to the invention.

| Coating composition | CrN Thin film | CrN Thick film | NbO | HfN | HfN | NbN |
|---|---|---|---|---|---|---|
| Technology | RCA | RCA | RPMS | RPMS | RPMS | RPMS |
| Set # | 1 | 3 | 2 | 4 | 5 | 6 |
| 17-4 Nom | X | X | X | X | X | X |
| 17-4 Low | X | X | X | X | NA | X |

TABLE 1-continued

Six example coatings according to the invention.

| Coating composition Technology Set # | CrN Thin film RCA 1 | CrN Thick film RCA 3 | NbO RPMS 2 | HfN RPMS 4 | HfN RPMS 5 | NbN RPMS 6 |
|---|---|---|---|---|---|---|
| 17-4 High | X | X | X | X | X | X |
| 420 Nom | X | X | X | X | X | X |
| 420 Low | X | X | X | X | X | X |
| 420 High | X | X | X | X | X | X |
| 465 Nom | X | X | X | NA | X | X |
| 465 Low | X | X | X | X | X | X |
| 465 high | X | X | X | X | X | X |

In Table 1, nom, low high, refer to the intensity of bead blast pressures used on coupons to generate different surfaces on the coupons that were subjected to the first round of coatings.

Example 2

Sample Analysis

Table 2 shows the results of sample analysis for the coating compositions shown in Table 1. The Calotte tester used a destructive tester for approximate coating thickness measurement on flat coupons (results summarized below). The Rockwell Diamler Benz test is a destructive coating adhesion/spalling test on flat coupons (results summarized below). The La wave tester is a modulus (elasticity) tester using laser induced acoustic waves (results summarized below).

The data in Table 2 shows that the advantageous properties of certain example coatings according to the invention. The HF values show generally good adhesion and spalling resistance.

TABLE 2

Coupon sample analysis for the coating compositions shown in Table 1.

| Coating Type | Calotto on S304 witness Thickness | Rockwell/Diamlar Benz Test on S304 Spalling/Adhesion level indicator | Density (g/Cm$^3$) | La Wave on witness(Si) Youngs Modulus (GPA) |
|---|---|---|---|---|
| CrN (Thin) | 3.8 | HF-1 | 6.2 | 320 |
| CrN (Thick) | 7.3 | HF 2-3 | 6.2 | 218 |
| NbO | 3 | HE 2-3 | 4.5 | 95 |
| HfO | 4.8 | HF-4 | 11.4 | 131 |
| HfN | 3 | HF 1-2 | 13.1 | 242 |
| NbN | 3.4 | HF 2 | 6.7 | 169 |

Example 3

Coatings Thickness Analysis

Figure 5A:
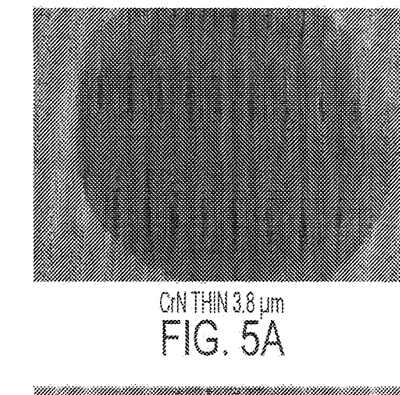
FIGS. 5A-F illustrate example coatings and their thicknesses test results.
Figure 5B:
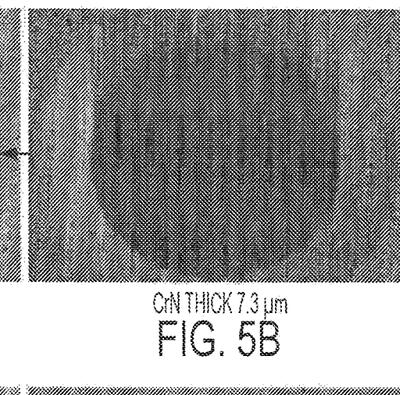
Figure 5C:
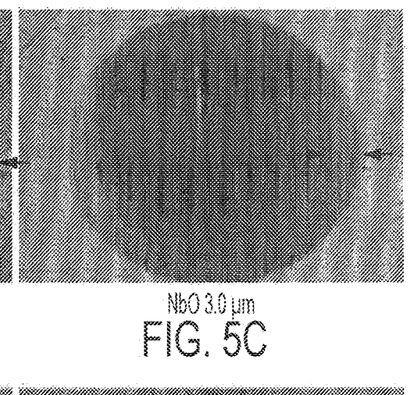
Figure 5D:
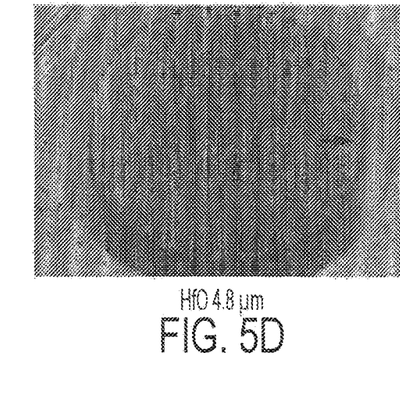
Figure 5E:
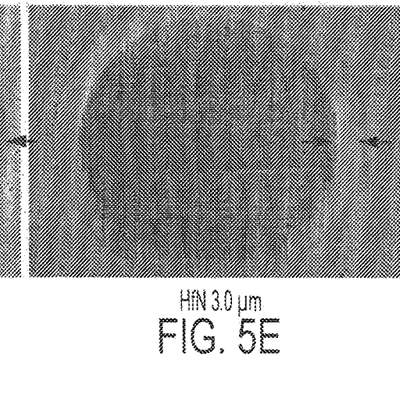
Figure 5F:
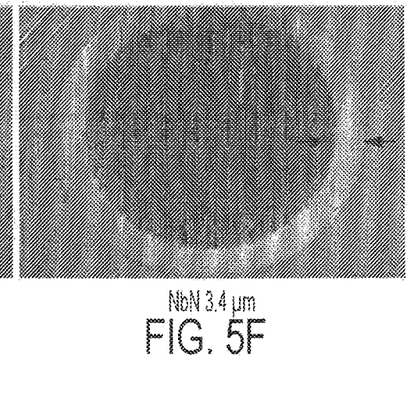

FIGS. 5A-F illustrate example coatings and their thicknesses test results. FIG. 5A illustrates a CrN thin film having a thickness of 3.8 μm (this and other thicknesses in FIGS. 5A-F indicated and the pairs of arrows). FIG. 5B illustrates a CrN thick film having a thickness of 7.3 μm. FIG. 5C illustrates a NbO coating having a thickness of 3.0 μm. FIG. 5D illustrates a HfO coating having a thickness of 4.8 μm. FIG. 5E illustrates a HfN coating having a thickness of 3.0 μm. FIG. 5F illustrates a NbN coatings having a thickness of 3.4 μm.

Example 4

Coatings Adhesion and Spalling Analysis

Figure 6A:
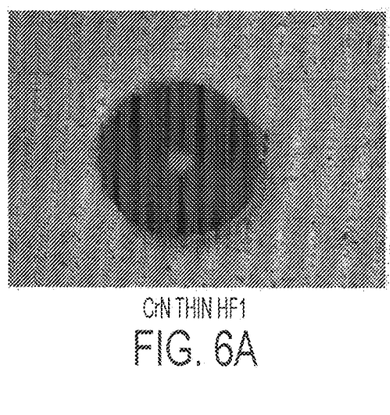
FIGS. 6A-F illustrate example coatings and their Rockwell/Diamlar Benz test results.
Figure 6B:
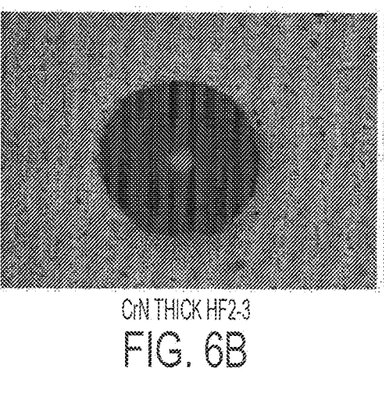
Figure 6C:
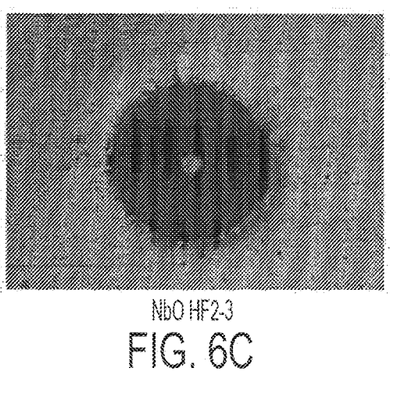
Figure 6D:
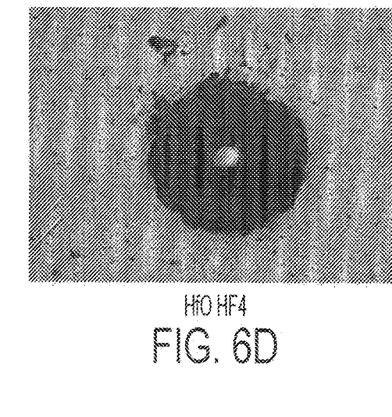
Figure 6E:
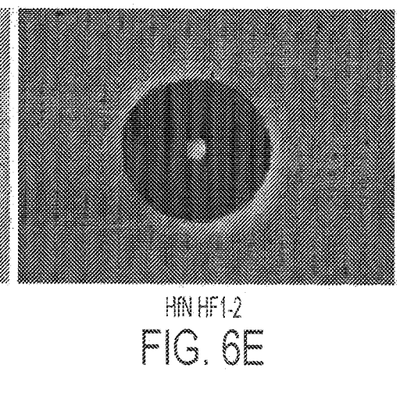
Figure 6F:
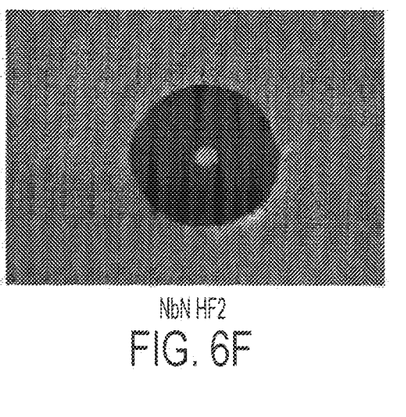

FIGS. 6A-F illustrate example coatings and their Rockwell/Diamlar Benz test results. FIG. 6A illustrates a CrN thin film having an adhesion/spalling of HF1. FIG. 6B illustrates a CrN thick film having an adhesion/spalling of HF2-3. FIG. 6C illustrates an NbO coating an adhesion/spalling of HF2-3. FIG. 6D illustrates an HfO coating having an adhesion/spalling of HF4. FIG. 6E illustrates an HfN coating having an adhesion/spalling of HF1-2. FIG. 6F illustrates an NbN coatings having an adhesion/spalling of HF2. The coatings show good lamination, with the CrN thin film and HfN coating having the relatively most robust coating under the given test conditions. (Data from Table 2 and discussed in Example 2 above.)

The instrument disclosed herein can be used in surgery, for example as spine surgical instruments and spinal implants. While the instruments disclosed herein may be generally described in the context spinal surgery, it will be appreciated that they can be used with any human or animal implant, in any of a variety of surgeries performed on humans or animals, and/or in fields unrelated to implants or surgery.

A person of ordinary skill in the art will appreciate further features and advantages of the invention based on the above-described embodiments and objectives. Accordingly, the invention is not to be limited by what has been particularly shown and described, except as indicated by the appended claims or those ultimately provided. All publications and references cited herein are expressly incorporated herein by reference in their entirety, and the invention expressly includes all combinations and sub-combinations of features included above and in the incorporated reference.

The invention claimed is:

1. A method for manufacturing a coated medical instrument comprising:
    depositing a first layer on a metal substrate surface of a medical instrument by vapor deposition, the first layer comprising chromium (Cr), hafnium (Hf), titanium (Ti), and/or niobium (Nb);
    depositing a second layer on the first layer by vapor deposition, the second layer bonded to the first layer, and the second layer comprising a nitride, oxide, carbide, carbonitride, or boride of chromium (Cr), hafnium (Hf), niobium (Nb), tungsten (W), titanium (Ti), aluminum (Al), zirconium (Zr), and/or silicon (Si); and
    depositing a third layer on the second layer by vapor deposition, the third layer comprising a nitride, oxide, carbide, boride, oxynitride, oxycarbide, or oxycarbonitride of chromium (Cr), hafnium (Hf), niobium (Nb), tungsten (W), titanium (Ti), aluminum (Al), zirconium (Zr), and/or silicon (Si);
    wherein the method further comprises a reactive plasma surface cleaning-conditioning process before depositing at least one of the first, second, and third layers.

2. The method of claim 1, wherein at least one of the layers is deposited by an arc process or a combination of an arc and sputter processes.

3. The method of claim 1, wherein at least one of the layers is deposited at a temperature of 180 to 1,000° F.

4. The method of claim 1, further comprising external cleaning the metal substrate surface before depositing the first layer.

5. The method of claim 1, further depositing the second layer using an arc and sputter process, thereby depositing a gradient in the second layer.

6. The method of claim 1, further comprising depositing the first and second layers in a first vapor deposition chamber and depositing the third layer in a second vapor deposition chamber.

7. The method of claim 1, wherein the coated medical instrument is corrosion resistant.

8. A method for manufacturing a coated medical instrument comprising:
    depositing a first layer on a metal substrate surface of a medical instrument by vapor deposition, the first layer comprising chromium (Cr), hafnium (Hf), titanium (Ti), and/or niobium (Nb);
    depositing a second layer on the first layer by vapor deposition, the second layer bonded to the first layer, and the second layer comprising a nitride, oxide, carbide, carbonitride, or boride of chromium (Cr), hafnium (Hf), niobium (Nb), tungsten (W), titanium (Ti), aluminum (Al), zirconium (Zr), and/or silicon (Si); and
    depositing a third layer on the second layer by vapor deposition, the third layer comprising a nitride, oxide, carbide, boride, oxynitride, oxycarbide, or oxycarbonitride of chromium (Cr), hafnium (Hf), niobium (Nb), tungsten (W), titanium (Ti), aluminum (Al), zirconium (Zr), and/or silicon (Si);
    wherein the method further comprises cleaning and conditioning a surface of the second layer using a plasma cleaning technique before depositing the third layer.

9. The method of claim 8, wherein at least one of the layers is deposited by an arc process or a combination of an arc and sputter processes.

10. The method of claim 8, wherein at least one of the layers is deposited at a temperature of 180 to 1,000° F.

11. The method of claim 8, further comprising external cleaning the metal substrate surface before depositing the first layer.

12. The method of claim 8, further depositing the second layer using an arc and sputter process, thereby depositing a gradient in the second layer.

13. The method of claim 8, further comprising depositing the first and second layers in a first vapor deposition chamber and depositing the third layer in a second vapor deposition chamber.

* * * * *